(12) United States Patent
Zucchi et al.

(10) Patent No.: US 8,226,881 B2
(45) Date of Patent: Jul. 24, 2012

(54) DIE FOR MOLDING OF A CUFF ON A PLASTIC TUBE

(75) Inventors: Giuseppe Zucchi, S. Possidonio (IT); Daniele Resca, San Felice Sul Panaro (IT); Alessandra Pedarzini, Finale Emilia (IT)

(73) Assignee: Covidien AG, Neuhausen am Rheinfall (CH)

( * ) Notice: Subject to any disclaimer, the term of this patent is extended or adjusted under 35 U.S.C. 154(b) by 69 days.

(21) Appl. No.: 12/556,826

(22) Filed: Sep. 10, 2009

(65) Prior Publication Data
US 2010/0194001 A1 Aug. 5, 2010

(30) Foreign Application Priority Data
Feb. 5, 2009 (IT) ............... BO2009A0054

(51) Int. Cl.
*B29C 49/64* (2006.01)
(52) U.S. Cl. ........... 264/515; 249/79; 264/523; 425/526
(58) Field of Classification Search ............ 425/526; 249/79; 264/515, 523
See application file for complete search history.

(56) References Cited

U.S. PATENT DOCUMENTS

| | | | | |
|---|---|---|---|---|
| 237,168 A | * | 2/1881 | Carpenter | 264/535 |
| 2,326,041 A | * | 8/1943 | Lavallee | 264/526 |
| 3,454,988 A | * | 7/1969 | Cremer | 425/233 |
| 3,704,081 A | * | 11/1972 | Immel | 425/4 R |
| 5,181,505 A | * | 1/1993 | Lew et al. | 128/200.26 |
| 5,236,659 A | | 8/1993 | Pinchuk et al. | |
| 5,330,345 A | | 7/1994 | Strock et al. | |
| 2005/0137615 A1 | * | 6/2005 | Mapes et al. | 606/159 |
| 2007/0088378 A1 | | 4/2007 | Okushi et al. | |

FOREIGN PATENT DOCUMENTS

| | | |
|---|---|---|
| GB | 1 451 469 A | 10/1976 |
| GB | 1 557 849 A | 12/1979 |
| GB | 2 102 528 A | 2/1983 |

OTHER PUBLICATIONS

Italian Search Report for Appln. No. IT BO20090054 completed Nov. 19, 2009.
European Search Report for Appln. No. 09010544.6 completed Jun. 21, 2010.
European Search Report for Appln. No. 08 42 5760 completed Jun. 12, 2009.

\* cited by examiner

*Primary Examiner* — Robert B Davis

(57) ABSTRACT

A die for molding a cuff on a plastic tube, including an upper shell and a lower shell defining a molding cavity between them; each of the shells has an external structure and an internal wall for defining a half of the molding cavity and for defining a hollow space with the external structure. The molding cavity and hollow spaces are separated from each other by internal walls. The die includes openings which are connected with the molding cavity and the hollow spaces respectively.

18 Claims, 5 Drawing Sheets

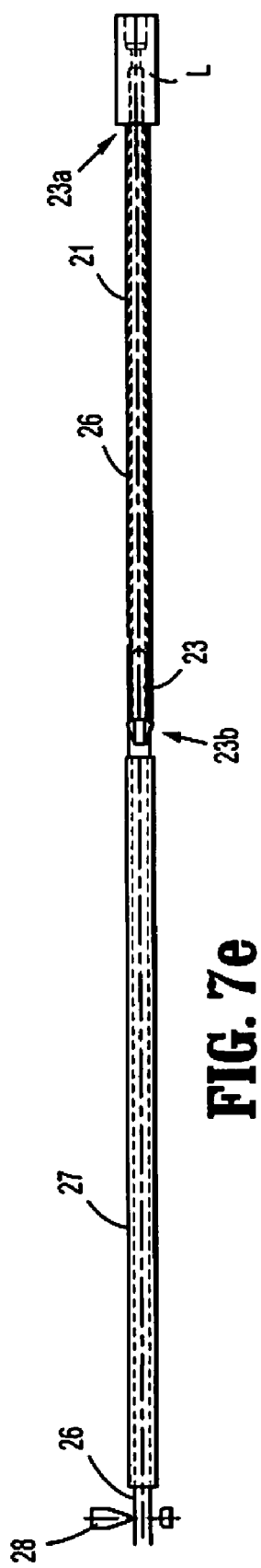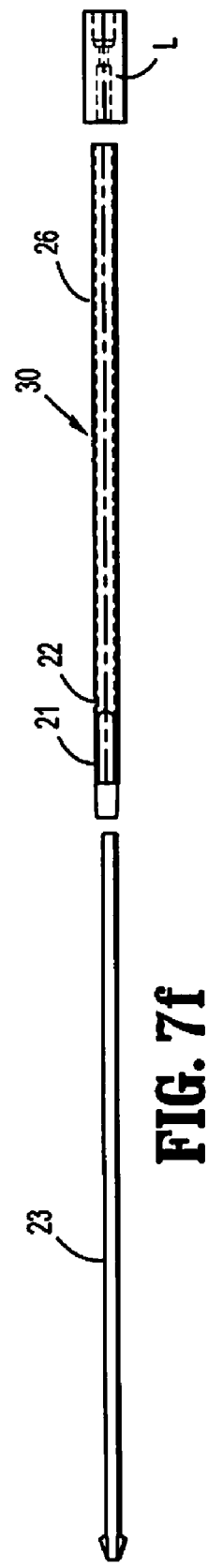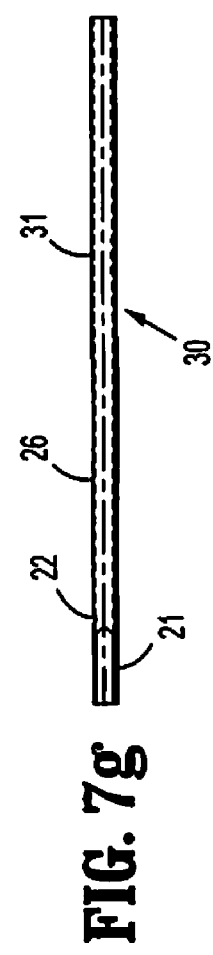

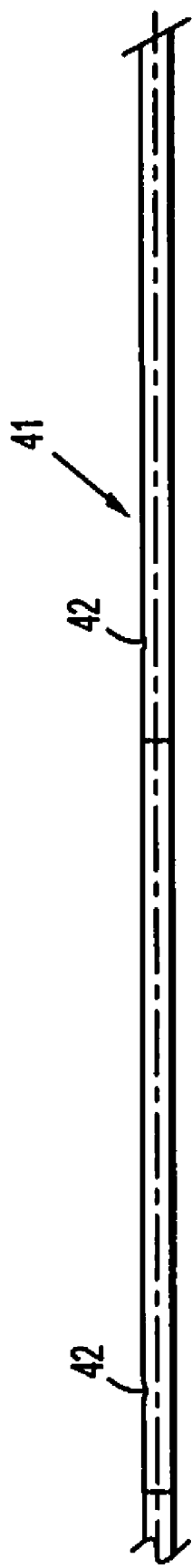
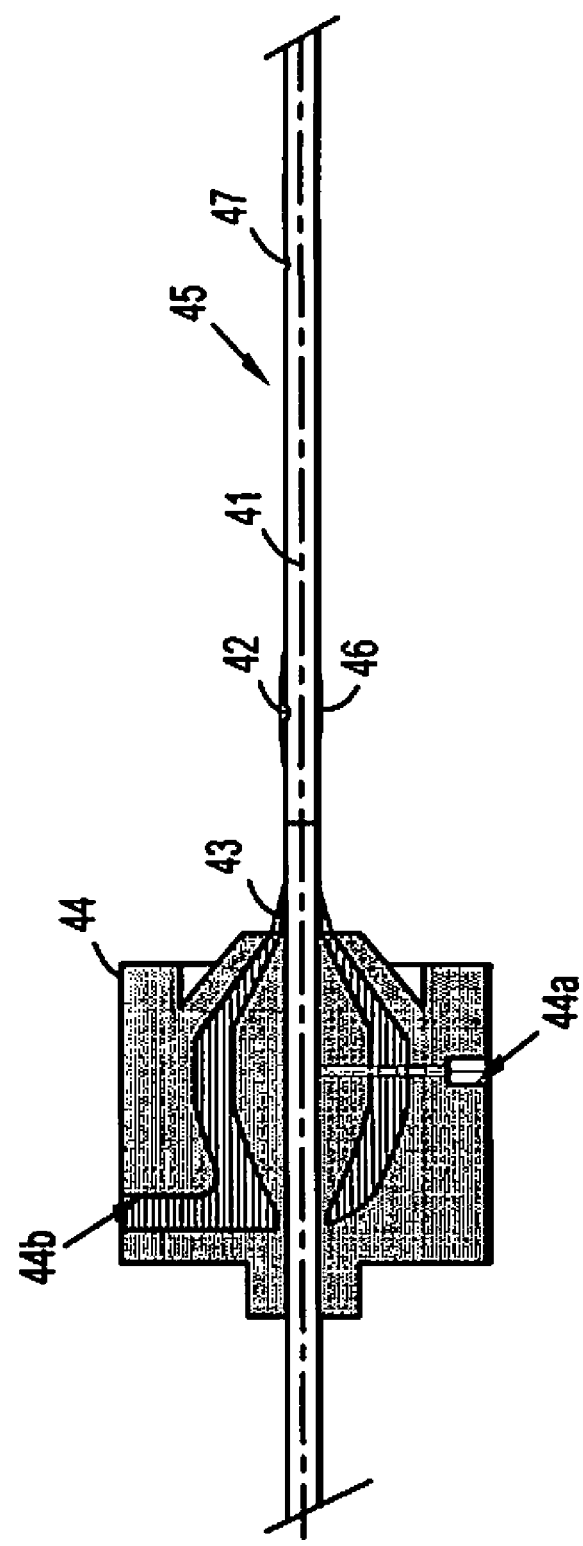

DIE FOR MOLDING OF A CUFF ON A PLASTIC TUBE

TECHNICAL FIELD

The present disclosure concerns a die for molding a cuff on a plastic tube. In particular, the die of the present disclosure is used for molding a cuff on a tracheal tube or a tracheostomy cannula.

BACKGROUND

As used herein, the term "cuff" is intended to mean an inflatable balloon attached around a tube, e.g. a tracheal tube. In tracheal tubes the purpose of the cuff is to function as a seal between the tube and the trachea in order to prevent air from getting out and bacteria entering the lungs. In other catheters, e.g. urine catheters, the purpose of the cuff is to block and secure the tube in the body part where it is inserted into.

Tracheal tubes are used for conveying air or gas mixtures delivered by an Intensive Care Unit or Anaesthesia ventilator, through a breathing circuit, into the patient airways. Tracheostomy cannulas can have the same use as tracheal tubes or can be installed on spontaneously breathing patients who for a particular disease or accidental reasons cannot breath autonomously and sufficiently without this airway bypass.

Conventionally, the cuff is obtained through a blowing process or via pre-extruded tubing expansion. The assembly process of the cuff on the tube consists of the following phases: cutting of the cuff ends, named collars; insertion of the cuff on the tube and correcting its positioning; and gluing with solvents or adhesive.

The result obtained from the above process is the formation of a kind of step similar to the collar cutting edge. This step represents a traumatic factor during intubation operation because of the possible abrasions it can cause. This problem is particularly relevant for children and infant patients where the diameter of the tubes is narrower and the collar thickness is crucial.

Another problem of the prior art process relates to the shaping and the assembly operations in manufacturing rendering the whole process slow, expensive and relying heavily on personnel experience and ability. It is important to notice that such problems become more relevant when the tube has a narrow diameter (e.g. for children and infant patients) and when the cuffs are made of polyurethane (PU) with reduced thickness and can be easily damaged during handling, tubing and gluing.

Another way to form a cuff on a tracheal tube is disclosed in for example, EP1733752, the entire contents of which is hereby incorporated by reference, which provides the production of silicon catheters having an antibonding agent in the zone of the cuff shaping which would entail inefficient time and high cost problems.

Accordingly, there is a need for forming a die for molding cuffs on plastic tubes whose technical characteristics are such that molding is simple and effective.

SUMMARY

A die for molding a cuff on a plastic tube is provided wherein the die includes an upper shell; and a lower shell defining a molding cavity between the upper and lower shell for insertion therein of the plastic tube; wherein each of the shells has an external wall structure and an internal wall, the internal wall of a respective shell defining a half of the molding cavity and the external wall structure and the internal wall of each shell defining a hollow space there between; the molding cavity and the hollow spaces being separated from each other by the internal walls; and the die having openings which are connected with the molding cavity and the hollow spaces respectively.

A molding process for manufacturing a cuff on a plastic tube with a die according to the present disclosure is provided which includes: inserting a tube in a molding cavity such that it is tightly housed; softening a portion of a sheath of the tube with a fluid; molding a portion of softened sheath to the internal walls; and stiffening a portion of softened sheath adhered to the internal walls with a second fluid.

BRIEF DESCRIPTION OF THE DRAWINGS

Various embodiments of the present disclosure will be described herein below with reference to the figures wherein:

FIGS. 7*a*-7*g* show the manufacture of a tube for use with the die of the present disclosure; and FIGS. 8*a*-8*b* show an alternative method of manufacture of the tube for use with the die of the present disclosure.

DETAILED DESCRIPTION

In embodiments, the present disclosure provides a die for molding cuffs on plastic tubes including an upper shell; and a lower shell defining a molding cavity between the upper and lower shell for the insertion therein of the plastic tube; wherein each of the shells has an external wall structure and an internal wall, the wall of a respective shell defining a half of the molding cavity and the wall structure and the wall of each shell defining a hollow space there between; the molding cavity and the hollow spaces being separated from each other by the internal walls; the die having openings which are connected with the molding cavity and the hollow spaces respectively.

In embodiments, a molding process for manufacturing a cuff on a plastic tube by a die of the present disclosure is provided which includes: inserting a tube in a molding cavity such that it is tightly housed; softening a portion of the sheath of the tube with a fluid; molding a portion of softened sheath to the internal walls; and stiffening the portion of softened sheath adhered to the internal walls with a second fluid.

For a better understanding of the present disclosure the following embodiments are described, only in an exemplificative and not limitative way, with reference to the figures.

Figure 1:
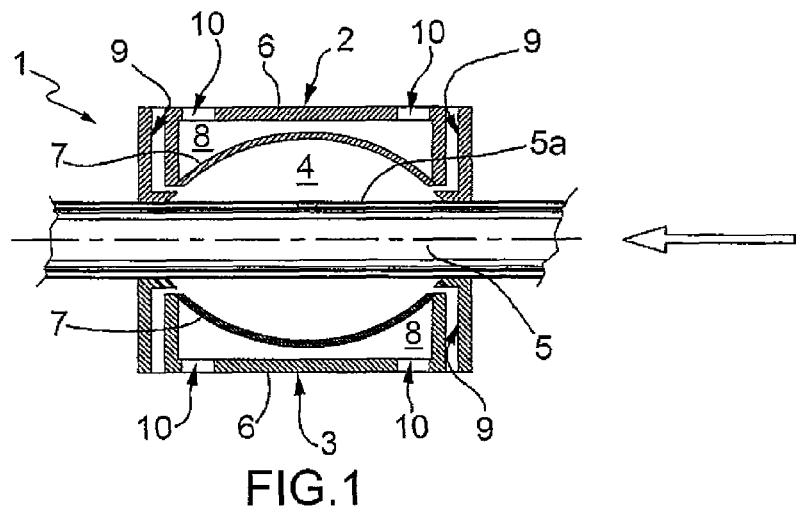
FIGS. 1-6 show the die of the present disclosure during six different manufacturing steps.

In FIG. 1, a die of the present disclosure as a whole is illustrated with the reference number 1. The die 1 includes an upper shell 2 and a lower shell 3, which can be coupled in order to form a molding cavity 4, wherein a portion of a tube 5 is fluid-tightly housed in order to manufacture the cuff.

Each shell 2 and 3 includes an external box structure 6 and an inner wall 7, having a semi-ovoid shape and closing the external box structure 6. The internal wall 7 delimits the half of the molding cavity 4. Between the external box structure 6 and the internal wall 7, is defined a hollow space 8. In the external box structure, a first plurality of canalizations 9 is formed connecting the molding cavity 4 to the outside, and a second plurality of canalizations 10 is formed connecting the hollow space 8 to the outside.

Referring now to FIGS. 2-6, the use of the die of the present disclosure is described below.

Figure 2:
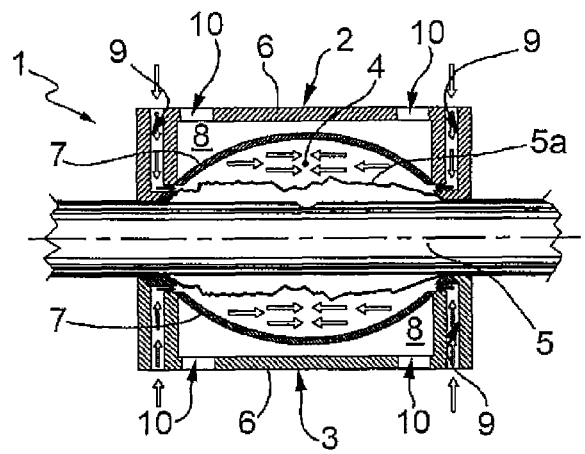

As shown in FIG. 2, a hot liquid is injected through canalizations 9 into the molding cavity 4, which houses the portion of tube 5 to be molded. The hot liquid comes into contact with a portion of the sheath of the tube 5 for softening it in order to be able to model it. In particular, the sheath 5a does not adhere to the underlying tube because of the air between the contact surfaces, as will be described below.

Figure 3:
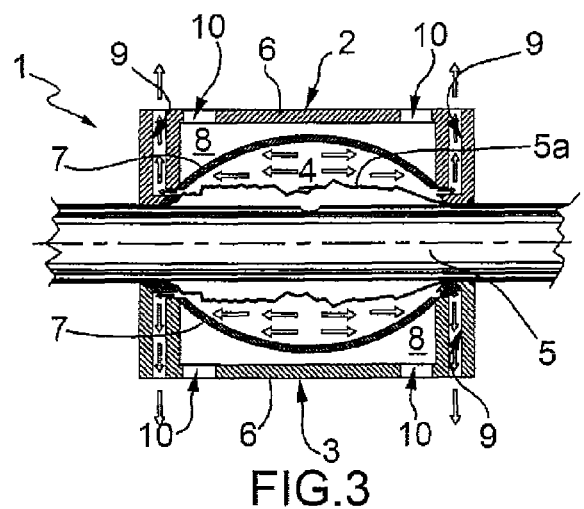

Once a pre-determined period of time, sufficient for the softening of the sheath 5a, has elapsed, the hot liquid is extracted through the same canalizations 9 as shown in FIG. 3, by a light vacuum. During the extraction of the hot liquid, the portion of softened sheath 5a is suctioned towards the internal wall 7, shaping itself thereon.

Figure 4:
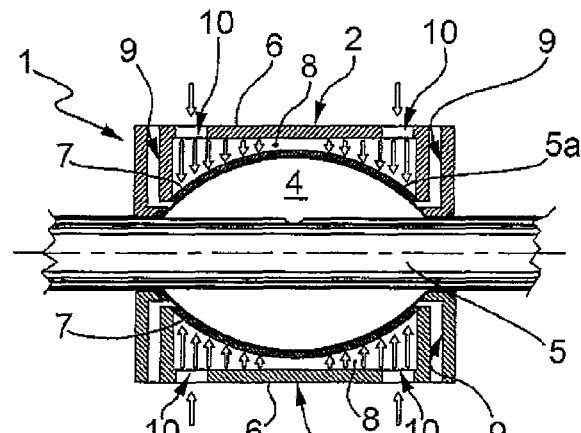

A cold liquid is then inserted into the hollow space 8 through canalizations 10, as shown in FIG. 4. The cooling due to the cold liquid on the internal wall 7 stiffens the portion of sheath 5a, thus allowing it to form its final shape.

Figure 5:
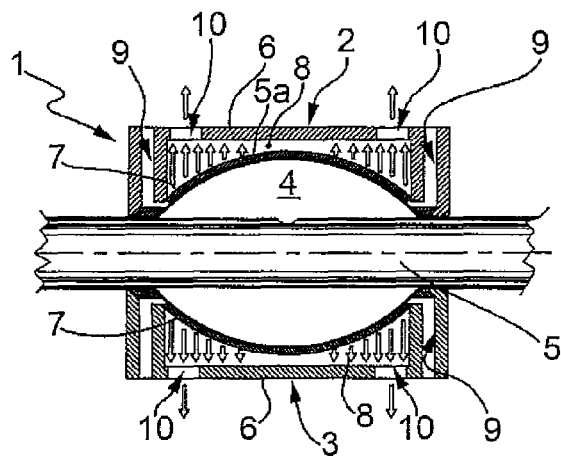
Figure 6:
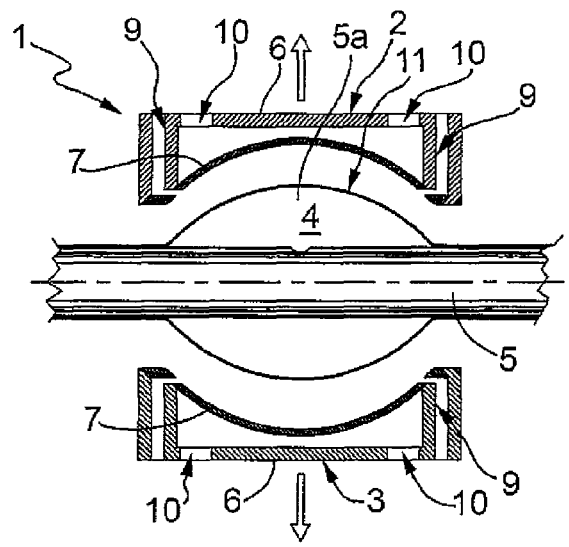

Once the portion of sheath 5a has formed its final shape, the cold liquid is extracted through canalizations 10 as shown in FIG. 5, and the die is opened (see FIG. 6) for extracting the tube 5 whereon the cuff 11 is formed.

For providing a more complete understanding of the present disclosure, the manufacture of a tracheal tube for use with the die of the present disclosure will now be described.

Figure 7A:

FIG. 7a illustrates a tracheal tube, extruded and successively cut at a desired length, indicated as 21. A superficial incision 22 has been cut out on the tracheal tube 21 to connect an inflation lumen (not shown) to the outside in relation to the cuff to be provided as described below.

Figure 7B:
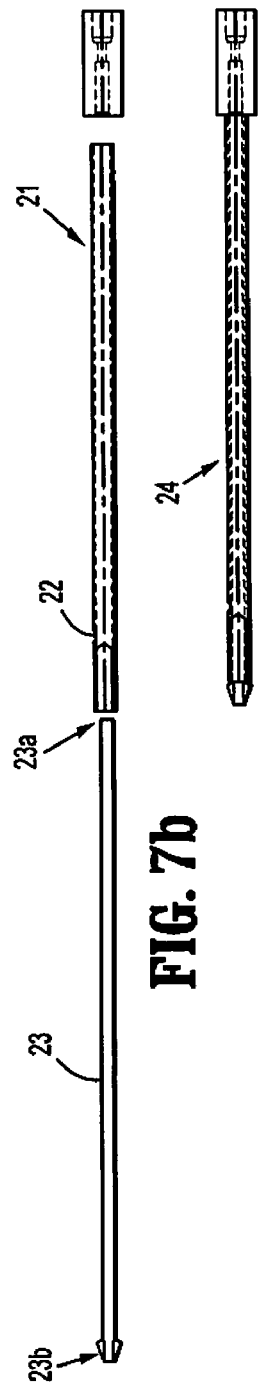

FIG. 7b shows a metal core 23 around which the tracheal tube 21 is placed to form an assembly 24. In particular, the metal core 23 is hollow and includes a connecting end 23a to be connected to a feeding line for compressed air L, and a truncated conical end 23b having some holes (not shown) for the outlet of the compressed air. As shown, the second end 23b having a truncated conical shape remains outside the tracheal tube 21.

Figure 7C:
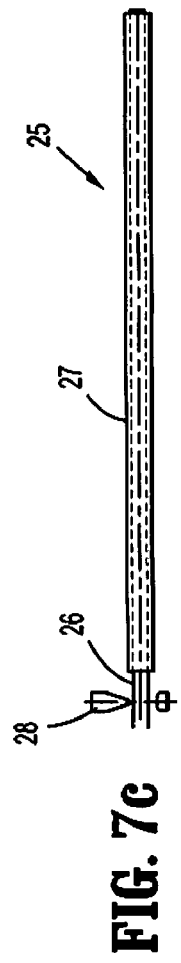

FIG. 7c shows a second assembly 25 including an extruded and cooled sheath 26 inserted inside a metal tube 27. The position of the sheath 26 in the tube 27 is kept fixed by a clamp 28. In particular, the metal tube 27 has an inner diameter larger than the diameter of the sheath 26, so that the sheath 26, once inflated, can take on the size of the metal tube 27.

Figure 7D:
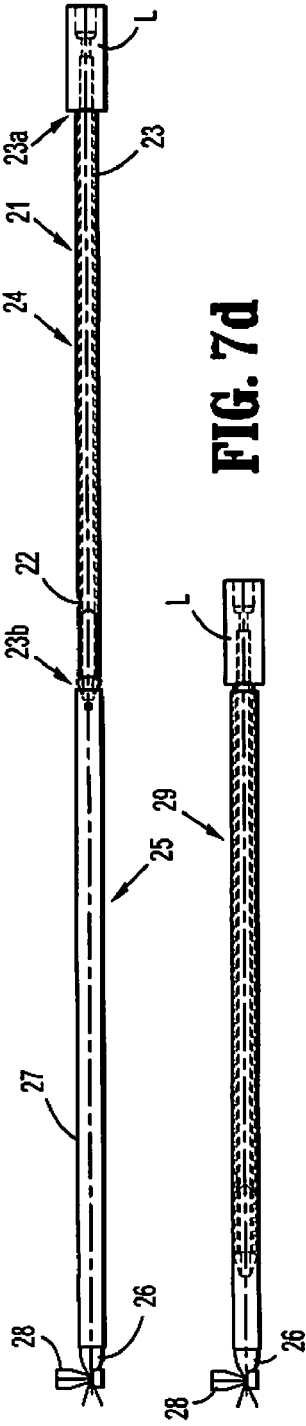

As shown in FIG. 7d, the assembly 25 is connected to the assembly 24 by bringing the truncated conical end 23b inside a first end of the sheath 26. The air injection through the truncated conical end 23b starts in this position, while at the same time the assembly 24 slides inside the assembly 25 obtaining a new assembly 29. During the sliding of the assembly 24 inside the assembly 25, the outcoming air inflates the sheath 26 and keeps it adherent to the metal tube 27 by simultaneously forming an air cushion around the tracheal tube 21. The air cushion then allows the tracheal tube 21 to slide into the sheath 26, which, having an inner diameter smaller than the outer diameter of the tube and being made of an elastic material, stays adherent to the tracheal tube 21 as soon as the air cushion collapses.

FIG. 7e shows the splitting up of the assembly 29 once the sheath 26 has completely adhered to the tracheal tube 21. The splitting up occurs by releasing the clamp 28 and extracting from the metal tube 27 the tracheal tube 21 and the sheath 26 surrounding it. Once extracted, the portion of sheath 26 is cut in relation to the truncated conical end 23b, while inside the metal tube 27 a new portion of sheath 26 is placed for a new production cycle.

FIG. 7f shows the detachment of the metal core 23 from the tracheal tube 21, while the sheath 26 undergoes a finishing cut for adapting it to the size of the tracheal tube 21, thus obtaining the semifinished product of medical tube 30.

FIG. 7g shows the semifinished product 30 whereon an incision 31 is cut out for connecting in use the inflation lumen with a portion of the inflation tube it will be glued onto. The semifinished product 30 is suitable for insertion into the die 1 of the present disclosure.

With a reference to FIGS. 8a-8b, a second method for the manufacture of a tracheal tube is shown, which differs from the one relating to FIGS. 7a-7g because of its larger automation.

FIG. 8a shows a continuously extruded tracheal tube 41, cooled with air and on which a superficial incision 42 is cut out at a predefined distance for connecting the inflation lumen (already known and not shown for the sake of simplicity) to the cuff to be provided as described hereinafter. The tracheal tube 41 has such a stiffness that it does not need a metal core as was needed in the embodiments of FIG. 7.

FIG. 8b shows a covering step of the tracheal tube 41 with a sheath 43. Once cooled and incised as previously described, the tracheal tube 41 is continuously inserted in a second extrusion head 44 by means of which the covering sheath 43 is produced by overextrusion. In particular, plastic material enters the extrusion head 44 through an inlet 44b and is overextruded around tube 41 forming the sheath 43. During the overextrusion of the sheath 43, some air is injected at regular intervals between the tracheal tube 41 and the forming sheath 43. In particular, the air enters the extrusion head 44 through an inlet 44a, in use connected to a feeding line of compressed air, and is injected in relation to the superficial incisions 42 between the sheath 43 and the tracheal tube 41 so that some non-adhesion areas are formed around the incisions 42. Thus, a semifinished medical tube 45 is obtained including a regularly distributed plurality of swellings 46 of the sheath 43 in the areas around the incisions 42. Afterwards, regularly distributed incisions 47 are cut out for connecting in use the inflation lumen to respective portions of the inflation tube they will be glued onto.

Accordingly, the die of the present disclosure is particularly simple, both in its manufacture and in its use. In addition, the die of the present disclosure can be advantageously used in plastic tubes which have been covered with a sheath having antimicrobial activity.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. Die for molding a cuff on a plastic tube, the die comprising:
   an upper shell;
   a plastic tube including an outer sheath, the outer sheath being radially expandable; and
   a lower shell defining a molding cavity between the upper and lower shell for insertion therein of the plastic tube;
   wherein each of the shells has an external wall structure and an internal wall, the internal wall of a respective shell defining a half of the molding cavity and the external wall structure and the internal wall of each shell defining a hollow space there between; the molding cavity and the hollow spaces being separated from each other by the internal walls; and the die having a first opening connecting the molding cavity to an external environment, and a second opening connecting the hollow spaces to the external environment, the first opening being different from the second opening; the upper shell and the lower shell configured to be separable from each other to allow removal of the plastic tube with the cuff formed thereon.

2. Die according to claim 1, wherein the molding cavity and the hollow spaces are configured to be occupied by a fluid which is inserted and extracted through the openings.

3. Die according to claim 2, wherein the fluid is a liquid.

4. Die according to claim 1, wherein the external wall structure has a box shape.

5. Die according to claim 1, wherein the internal wall has a semi-ovoid shape.

6. Die according to claim 1, wherein the plastic tube is a medical tube.

7. Die according to claim 6, wherein the medical tube is selected from the group consisting of a tracheal tube, a tracheostomy cannula, and the like.

8. Molding process for manufacturing a cuff on a plastic tube with a die according to claim 1; the process comprising the steps of: inserting a tube in a molding cavity such that it is tightly housed; softening a portion of a sheath of the tube with a fluid; molding a portion of softened sheath to the internal walls; and stiffening a portion of softened sheath adhered to the internal walls with a second fluid.

9. Molding process according to claim 8, wherein the softening step includes injecting a fluid into the molding cavity for contacting and softening the sheath.

10. Molding process according to claim 9, wherein the fluid is a hot liquid.

11. Molding process according to claim 10, wherein the stiffening step includes a second fluid injected into a hollow space of the die such that the sheath adhered to the internal walls are stiffened.

12. Molding process according to claim 11, wherein the second fluid is a cold liquid.

13. Molding process according to claim 9, wherein the molding step includes the step of suctioning out the fluid used in the softening step.

14. Molding process according to claim 13, wherein the molding step includes suctioning out the fluid through the openings with a light vacuum.

15. Die according to claim 1, wherein the molding cavity defines a passage, the plastic tube extending through the passage.

16. Die according to claim 1, wherein the outer sheath is separable from the plastic tube.

17. Die according to claim 1, wherein the outer sheath is spaced away from the plastic tube.

18. Die according to claim 17, wherein a fluid is disposed between the plastic tube and the outer sheath.

* * * * *